US005352570A

United States Patent [19]

Begley

[11] Patent Number: 5,352,570

[45] Date of Patent: Oct. 4, 1994

[54] METHOD AND PHOTOGRAPHIC MATERIAL AND PROCESS COMPRISING A BENZOTRIAZOLE COMPOUND

[75] Inventor: William J. Begley, Webster, N.Y.

[73] Assignee: Eastman Kodak Company, Rochester, N.Y.

[21] Appl. No.: 723,346

[22] Filed: Jun. 28, 1991

[51] Int. Cl.$^5$ .............................................. G03C 7/305

[52] U.S. Cl. .................................... 430/544; 430/553; 430/957

[58] Field of Search ........................ 430/544, 957, 553

[56] References Cited

U.S. PATENT DOCUMENTS

| | | | |
|---|---|---|---|
| 3,227,554 | 1/1966 | Barr et al. | 96/55 |
| 3,617,291 | 11/1971 | Sawdey | 430/553 |
| 4,248,962 | 2/1981 | Lau | 430/282 |
| 4,409,323 | 10/1983 | Sato et al. | 430/544 |
| 4,477,563 | 10/1984 | Ichijima et al. | 430/544 |
| 4,725,529 | 2/1988 | Shimazaki et al. | 430/505 |
| 4,798,784 | 1/1989 | Kishimoto et al. | 430/382 |
| 4,804,619 | 2/1989 | Yamada et al. | 430/505 |
| 4,812,389 | 3/1989 | Sakanoue et al. | 430/382 |
| 4,830,954 | 5/1989 | Matejec | 430/505 |
| 4,861,701 | 8/1989 | Burns et al. | 430/543 |
| 5,026,628 | 6/1991 | Begley et al. | 430/957 |
| 5,085,979 | 2/1992 | Yamagami et al. | 430/505 |
| 5,151,343 | 9/1992 | Begley et al. | 430/226 |
| 5,169,746 | 12/1992 | Sasaki | 430/957 |

FOREIGN PATENT DOCUMENTS

| | | | |
|---|---|---|---|
| 0283242 | 9/1988 | European Pat. Off. | 430/544 |

OTHER PUBLICATIONS

*Research Disclosure,* Dec. 1989, Item No. 308119, Kenneth Mason Publications Emsworth, Hampshire P010 7DQ, England.

*Primary Examiner*—Lee C. Wright
*Attorney, Agent, or Firm*—Peter C. Cody

[57] ABSTRACT

A new method of preparation of a single isomer of a benzotriazole compound comprises the step of reacting a benzotriazole compound containing symmetrical substituents on the benzo ring with phosgene to produce the corresponding carbamyl chloride. The carbamyl chloride can be reacted with a timeing group of a coupling-off group of a photographic coupler to form a photographic development inhibitor releasing coupler. Such compounds are useful in photographic materials and processes.

5 Claims, No Drawings

METHOD AND PHOTOGRAPHIC MATERIAL AND PROCESS COMPRISING A BENZOTRIAZOLE COMPOUND

This invention relates to a new method of preparation of a single isomer of a benzotriazole compound. The invention also relates to new photographic couplers prepared using such a method and to photographic materials and processes comprising such new photographic couplers.

Various photographic couplers are known in photographic materials and process. Such couplers upon oxidative coupling form dyes, such as cyan, magenta and yellow image dyes in the photographic materials and processes. Another class of such couplers are couplers that release a development inhibitor group for improvements in image formation during processing. Typically such couplers are development inhibitor releasing (DIR) couplers such as described in, for example, U.S. Pat. No. 3,227,554 and DIR coupler that have timing groups that enable timing of release of the development inhibitor group, such as described in, for example, U.S. Pat. Nos. 4,248,962; 4,409,323 and 4,861,701.

One class of such development inhibitor groups are benzotriazole development inhibitor groups. Benzotriazole development inhibitor groups on coupling off groups of development inhibitor releasing couplers have been found to provide for example, desired interimage effects and improved acutance in images. However, a problem we have encountered is that when benzotriazole compounds are synthesized for such materials an undesired mixture of isomers is produced. This mixture of isomers is the result of reactions occurring at all three nitrogen atoms of the benzotriazole nucleus.

It has been desirable to provide a process of forming such benzotriazole compounds that enables formation of a single isomer.

The present invention solves these problems by providing a method of preparation of a single isomer a benzotriazole derivative comprising the step of reacting a benzotriazole compound containing symmetrical substituents on the benzo ring with phosgene to produce the corresponding carbamyl chloride.

Such a process enables improved and simplified purification procedures and enables avoiding formation of compounds that can cause crystallinity problems.

The symmetrical substituents are preferably in the 5- and 6-positions of the benzo ring and are both either alkoxy, chlorine or bromine. The compounds wherein the 5- and 6-positions are both alkoxy are highly preferred.

The process as described is preferably carried in an organic solvent compatible with the reactants. Such organic solvents are typically toluene, methylene chloride, and tetrahydrofuran.

In the process when phosgene is used as described, the phosgene is added directly to the benzotriazole compound or is generated in situ by methods known in the organic synthesis art.

In a preferred embodiment of the process as described the process comprises reacting the carbamyl chloride formed with a timing group of a coupling-off group of a photographic coupler to form a photographic development inhibitor releasing coupler. Such an embodiment is especially useful for avoiding the formation of various isomers of the desired compounds.

A typical process as described of preparing a single isomer of a benzotriazole derivative represented by the formula:

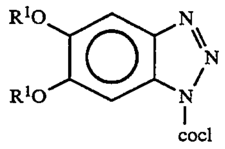

wherein $OR^1$ is alkoxy, such alkoxy comprising 1 to 10 carbon atoms; comprises reacting a benzotriazole compound represented by the formula:

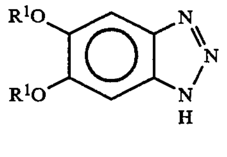

with phosgene.

The $OR^1$ is preferably alkoxy containing 1 to 5 carbon atoms, such as methyl, ethyl, i-propyl, s-propyl, n-propoxy, i-butoxy, t-butoxy, n-butoxy and the like.

A preferred method of preparing a photographic development inhibitor releasing coupler represented by the formula:

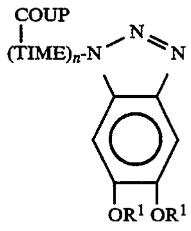

wherein COUP is a photographic coupler with the remainder of the molecule bonded at the coupling position; TIME is photographic timing group, particularly a timing group known in the photographic art; n is 0, 1 or 2; $OR^1$ is alkoxy as described; comprising reacting

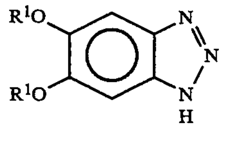

with phosgene; then reacting the resulting product with COUP-$(TIME)_n$. TIME is a timing group that can react with benzotriazole carbamoyl chloride without adversely affecting the remainder of the molecule.

An especially preferred method as described comprises such a process wherein COUP is a coupler capable in a photographic element upon exposure and processing of forming a dye capable of being washed out of the photographic element during processing.

A novel benzotriazole compound that can be prepared by the described process is represented by the formula:

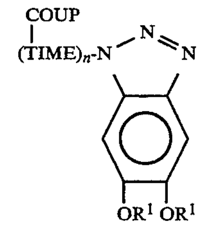

wherein COUP is a wash out type photographic coupler, such as a cyan, magenta or yellow dye-forming coupler, with the remainder of the molecule bonded to the coupling position of the coupler; TIME is a photographic timing group; n is 0, 1 or 2; $OR^1$ is alkoxy, as described. The coupler is preferably a wash out type naphtholic coupler comprising an amide group in the 2-position of the naphthol moiety.

The described reactions are typically carried out under ambient conditions of pressure, such as at atmospheric pressure at a temperature within the range of 0 to 100 degrees C. The temperature that is most useful will depend upon the reactants and the solvent used.

A benzotriazole development inhibitor group herein means any symmetrical benzotriazole development inhibitor group known in the photographic art, such as described in, for example, U.S. Pat. Nos. 4,477,563 and 4,812,389.

An illustrative synthesis according to the invention is as follows:

Synthesis Example A:

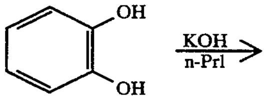

(1)

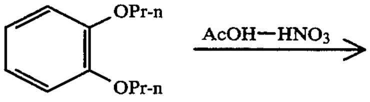

(2)

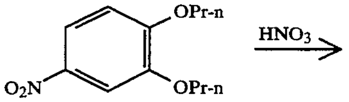

(3)

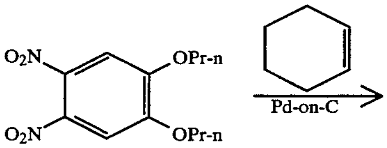

(4)

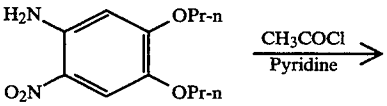

(5)

-continued

Synthesis Example A:

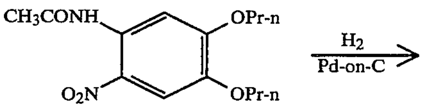

(6)

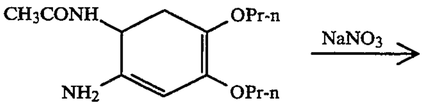

(7)

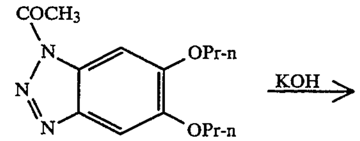

(8)

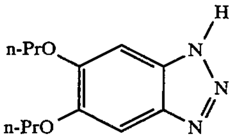

(9)

Experimental

Compound (2)

Compound (1), pyrocatechol, (25.0 g, 0.227 Mole), was dissolved in ethyl alcohol, (200 mL), to which was added n-propyl iodide, (81.0 g, 0.477 Mole) and the solution deoxygenated with a stream of nitrogen. This solution was heated gently on a steam bath while under nitrogen, and potassium hydroxide, (30.0 g of 85%, 0.454 mMole), added in small amounts with efficient stirring to keep the exothermic reaction mixture was stirred under nitrogen for 2 hours at reflux temperature. At the end of this period further quantities of potassium hydroxide, (15 g in 20 mL water) and n-propyl iodide, (40.0 g), were added and reflux with stirring under nitrogen continued. After a total time period of 4 hours the reaction mixture was cooled, filtered and the residue washed with a little cold ethyl alcohol. The combined ethyl alcohol solutions were then concentrated, treated with water, (500 mL), and extracted with ether, (×2). The ether extracts were then washed with 1N-KOH, (×3), water, (×1), and dried over $MgSO_4$. The solution was then filtered and concentrated under reduced pressure to give crude (2), which was of sufficient purity for the next step. Yield 29.0 g, 66%.

Compound (3)

Compound (2), (29.0 g, 0.149 Mole), as described above, was dissolved in acetic acid, (50 mL), and heated to 65° C. A solution of concentrated nitric acid, (20 mL), in acetic, (30 mL), was then added dropwise while maintaining the temperature in the range 65°–70° C. After the addition was complete, the orange/yellow solution was kept at 65° C. for approximately 30 minutes, then cooled, and poured into ice/water, (600 mL), with stirring. The yellow product which separated was filtered off, washed well with plenty of water and air dried. Yield of compound (3), 34 g, 95%.

Compound (4)

Compound (3), (34.0 g, 0.142 Mole), was suspended in concentrated nitric acid, (200 mL), and heated gently on a steam bath. At about 30°–40° C. the reaction exotherms. Heating was stopped until the exotherm had subsided and then heating continued with stirring, at 70° C. for 30 minutes. At the end of this period the reaction mixture was cooled and poured into ice-water with efficient stirring. The bright yellow product, compound (4), was filtered off, washed well with water and air dried. Yield, 35.0 g, 87%.

Compound (5)

compound (4) (10.0 g, 35.18 mMole), was dissolved in ethyl acetate, (100 mL), containing ethyl alcohol, (30 mL). To this solution was added 10%-Pd-on-C, (4.0 g), and cyclohexene, (22 mL). The resulting mixture was then refluxed for 1 hour. While hot, the solution was filtered over celite, cooled and concentrated under reduced pressure. The semi-solid which was obtained was treated with heptane and the yellow product, compound (5), filtered off and air-dried. Yield, 6.8 g, 78%.

Compound (6)

Compound (5), (14.3 g, 56.23 mMole), was dissolved in dry pyridine, (100 mL), cooled in an ice bath and acetyl chloride, (8 mL, 112.47 mMole), added dropwise with stirring. After all of the acetyl chloride had been added the reaction was allowed to come to room temperature over a 30 minute period. The reaction mixture was then poured into ice-cold 2N-HCl with efficient stirring and the product, compound (6), filter off, washed well with water and air-dried. Yield, 16.0 g, 96%.

Compound (7)

Compound 6), (11.0 g, 37.12 mMole), was dissolved in THF, (60 mL), and ethyl alcohol, (150 mL), added followed by 10%-Pd-on-C, (1.5 g). This solution was hydrogenated at 50 psi to give total conversion to the product in approximately 4 hours. The catalyst was filtered off and washed with a little THF. The combined washings and filtrate were concentrated under reduced pressure to yield compound (7), 100%.

Compound (8)

Compound (7), (20.0 g, 75.1 mMole), was dissolved in acetic acid, (250 mL), and water, (250 mL). This solution was cooled to 10°–15° C. and sodium nitrite, (6.74 g, 97.63 mMole), in water, (50 mL), added at such a rate as to keep the temperature between 10°–15° C. The reaction solution turned blue and the product, compound (8), crystallised out. After stirring at room temperature for 30 minutes the product was filtered off, washed well with water and air-dried to give 17.0 g, 80%, of crude product. The residual colour could be easily removed from the product by dissolving it in 50% ethyl acetate in heptane and passing it through a short pad of silica gel eluting with the same solvent mixture.

Compound (9)

Compound (8), (17.0 g, crude), was suspended in methanol, (100 mL), to which was added 1N-KOH, (150 mL, 150 mMole), and the suspension heated gently on a steam bath. After about 15 minutes when complete dissolution had been achieved, the solution was allowed to cool. Water, (150 mL), was then added and the pH of the solution adjusted to approximately 5 with 2N-HCl. The precipitated product was filtered off, washed with water and air dried. The crude material was dissolved in 60% ethyl acetate in toluene and passed through a short pad of silica gel eluting with the same solvent mixture. The main band was collected, concentrated to dryness under reduced pressure and recrystallised from ethyl acetate/heptane. Yield of compound (9), 9.0 g, 60%.

Combinations of the described couplers are also useful.

As used herein the term "coupler" refers rid the entire compound including the coupler moiety and the coupling-off group including the development inhibitor moiety. The term "coupler moiety" refers to that portion of the compound other than the coupling-off group.

Any photographic coupler moiety can be used for the coupler moiety of coupler (A), preferably a coupler moiety that upon oxidative coupling forms a dye that capable of being washed out of the photographic element upon processing. Typical photographic coupler moieties upon oxidative coupling form cyan, magenta or yellow dyes capable of being washed out of the element. Typical coupler moieties contain a water-solubilizing group, such as a —$COR^1$ wherein $R^1$ is typically $NHCH_3$, $NH_2$, $OCH_3$, $OC_2H_5$, $NHCH_2CH_2CO_2C_2H_5$, or groups substituted with carboxylic or sulfonic acid or hydroxy groups.

Preferred coupler moieties are naphtholic coupler moieties containing a substituent in the 2-position that is a water-solubilizing group that enables dye formed from the coupler upon oxidative coupling to be washed out of the element upon processing. Examples of such useful substituents —$COR^1$ in the 2-position of the naphtholic coupler include:

—$CONHCH_3$, —$CONH_2$, —$CONH(CH_2)$—J,

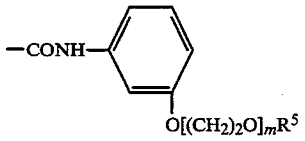

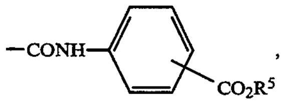

,

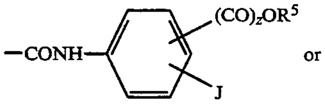

or

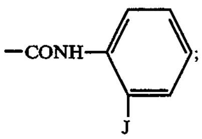

;

wherein $R^5$ is hydrogen methyl or ethyl and m is 1, 2 or 3; z is 0 or 1; and, J is —H, —CN, $SOR^5$, $SO_2R^5$, $CO_2R^5$, —Cl, —Br, or $OR^5$.

A preferred coupler, such as a naphtholic coupler, comprises in the coupling position a coupling-off group comprising in sequence a ballasted carbamate group and bonded to the carbamate group a releasable development inhibitor group. Examples of useful coupling-off groups that can be prepared as described include:

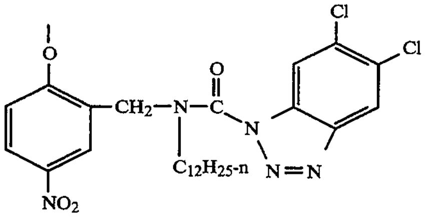

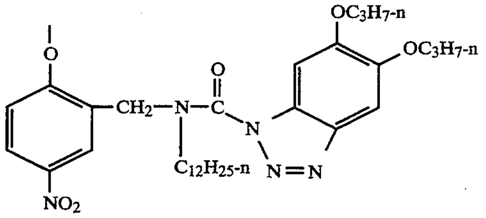

or

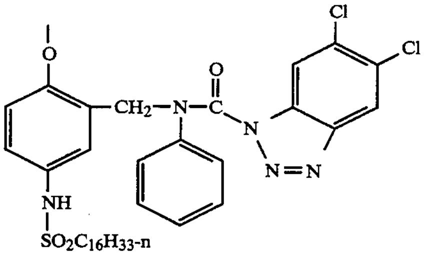

The coupler moiety can be monomeric, or it can be part of a dimeric, oligomeric or polymeric coupler in which case more than one group containing Z can be contained in the coupler.

The coupling-off group is joined to the coupler moiety at the coupling position of the coupler moiety. The coupling-off group is released from the coupling position by oxidative coupling reactions known in the photographic art.

Useful coupler moieties include, for example, those described in the following patents, preferably those in which the ballast groups on the coupler moieties are removed and replaced with water solubilizing groups as described above to enable the dyes formed from the coupler moieties to be washed out of the photographic element. In addition these patents and publications describe image dye-forming couplers that are useful in combination with the couplers of the invention:

I. COUP's

A. Couplers which form cyan dyes upon reaction with oxidized color developing agents are described in such representative patents and publications as: U.S. Pat. Nos. 2,772,162; 2,895,826; 3,002,836; 3,034,892; 2,474,293; 2,423,730; 2,367,531; 3,041,236; 4,333,999 and "Farbkuppler-eine Literaturübersicht," published in Agfa Mitteilungen, Band III, pp. 156–175 (1961).

Preferably such couplers are phenols and naphthols that form cyan dyes on reaction with oxidized color developing agent.

B. Couplers which form magenta dyes upon reaction with oxidized color developing agent are described in such representative patents and publications as: U.S. Pat. Nos. 2,600,788; 2,369,489; 2,343,703; 2,311,082; 3,152,896; 3,519,429; 3,062,653; 2,908,573 and "Farbkuppler-eine Literaturübersicht," published in Agfa Mitteilungen, Band III, pp. 126–156 (1961).

Preferably such couplers are pyrazolones and pyrazolotriazoles that form magenta dyes upon reaction with oxidized color developing agents.

C. Couplers which form yellow dyes upon reaction with oxidized and color developing agent are described in such representative patents and publications as: U.S. Pat. Nos. 2,875,057; 2,407,210; 3,265,506; 2,298,443; 3,048,194; 3,447,928 and "Farbkuppler-eine Literaturübersicht," published in Agfa Mitteilungen, Band III, pp. 112–126 (1961).

Preferably such yellow-dye forming couplers are acylacetamides, such as benzolyacetamides and pivaloylacetamides.

D. Couplers which form colorless products upon reaction with oxidized color developing agent are described in such representative patents as: U.K. Patent No. 861,138; U.S. Pat. Nos. 3,632,345; 3,928,041; 3,958,993 and 3,961,959.

Preferably such couplers are cyclic carbonyl containing compounds that form colorless products upon reaction with oxidized color developing agents.

The described image dye-forming couplers can be incorporated in the photographic element and/or in photographic processing solutions, such as developer solutions, so that upon development of the exposed photographic element they will be in reactive association with oxidized color developing agent. Couplers that are incorporated in photographic processing solutions should be of such molecular size and configuration that they will diffuse through photographic layers with the processing solution. When incorporated in the photographic element, the image dye-forming couplers and the couplers of the invention should be nondiffusible, that is they should be of such molecular size and configuration that they will not significantly diffuse or wander from the layer in which they are coated.

Upon processing, the image dye-forming coupler in the exposed areas of the photographic element typically forms an immobile dye image. However, a preferred coupler in the image areas forms a mobile dye that is capable of washing out of the element during processing.

Photographic elements of this invention can be processed by conventional techniques in which color forming couplers and color developing agents are incorporated in separate processing solutions or compositions or in the element. Photographic elements of this invention are especially useful as color negative elements that are processed in a conventional color negative photographic process.

Photographic elements in which the compounds of this invention are incorporated can be a simple element comprising a support and a single silver halide emulsion layer or they can be multilayer, multicolor elements. The compounds of this invention can be incorporated in at least one of the silver halide emulsion layers and/or in at least one of the silver halide emulsion layers and/or in at least one other layer, such as an adjacent layer, where they will come into reactive association with oxidized color developing agent which has developed silver halide in the emulsion layer. The silver halide emulsion layer can contain or have associated with it, other photographic coupler compounds, such as dye-forming couplers, colored masking couplers, and/or competing couplers. These other photographic couplers can form dyes of the same or different color and hue as the photographic couplers of this invention. Additionally, the silver halide emulsion layers and other layers of the photographic element can contain addenda conventionally contained in such layers.

A typical multilayer, multicolor photographic element can comprise a support having thereon a red-sensitive silver halide emulsion unit having associated therewith a cyan dye image-providing material, a green-sensitive silver halide emulsion unit having associated therewith a magenta dye image-providing material and a blue-sensitive silver halide emulsion unit having associated therewith a yellow dye image-providing material, at least one of the silver halide emulsion units having associated therewith a photographic coupler of the invention. Each silver halide emulsion unit can be composed of one or more layers and the various units and layers can be arranged in different locations with respect to one another.

The couplers of this invention can be incorporated in or associated with one or more layers or units of the photographic element.

The light sensitive silver halide emulsions can include coarse, regular or fine grain silver halide crystals or mixtures thereof and can be comprised of such silver halides as silver chloride, silver bromide, silver bromoiodide, silver chlorobromide, silver chloroiodide, silver chlorobromoiodide and mixtures thereof. The emulsions can be negative-working or direct-positive emulsions. They can form latent images predominantly on the surface of the silver halide grains or predominantly on the interior of the silver halide grains. They can be chemically and spectrally sensitized. The emulsions typically will be gelatin emulsions although other hydrophilic colloids are useful. Tabular grain light sensitive silver halides are particularly useful such as described in *Research Disclosure,* January 1983, Item No. 22534, U.S. Pat. No. 4,434,226 and U.S. application Ser. No. 419,177 filed Oct. 10, 1989.

The support can be any support used with photographic elements. Typical supports include cellulose nitrate film, cellulose acetate film, polyvinylacetal film, polyethylene terephthalate film, polycarbonate film and related films or resinous materials as well as glass, paper, metal and the like. Typically, a flexible support is employed, such as a polymeric film or paper support. Paper supports can be acetylated or coated with baryta and/or an α-olefin polymer, particularly a polymer of an α-olefin containing 2 to 10 carbon atoms such as polyethylene, polypropylene, ethylene-butene copolymers and the like.

The coupler of the invention can be used in a photographic element in the same way that photographic couplers that release a development inhibitor group have been used in the photographic art.

In the following discussion of suitable materials for use in the emulsions and elements of this invention, reference will be made to *Research Disclosure,* December 1978, Item 17643, published by Industrial Opportunities Ltd., Homewell Havant, Hampshire, P09 1EF, U.K., the disclosures of which are incorporated herein by reference. This publication will be identified hereafter by the term "Research Disclosure".

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents useful in the invention are p-phenylene diamines. Especially preferred are 4-amino-N,N-diethylaniline hydrochloride; 4-amino-3-methyl-N,N-diethyaniline hydrochloride; 4-amino-3-methyl-N-ethyl-N-β-(methanesulfonamido)ethylaniline sulfate hydrate; 4-amino-3-methyl-N-ethyl-N-β-hydroxyethylaniline sulfate; 4-amino-3-β-(methanesulfonamido)-ethyl-N,N-diethylaniline hydrochloride; and 4-amino-N-ethyl-N-(2-methoxyethyl)-m-toluidine di-p-toluenesulfonic acid.

With negative working silver halide, the processing step described above gives a negative image. To obtain a positive (or reversal) image, this step can be preceded by development with a non-chromogenic developing agent to develop exposed silver halide, but not form a dye, and then uniformly fogging the element to render unexposed silver halide developable. Alternatively, a direct positive emulsion can be employed to obtain a positive image.

The described photographic materials and processes can be used with photographic silver halide emulsions and addenda known to be useful in the photographic art, as described in, for example, *Research Disclosure,* December 1989, Item No. 308,119, the disclosures of which are incorporated herein by reference.

An especially useful embodiment of the invention is a color photographic element comprising a support bearing at least one photographic silver halide emulsion layer and at least one benzotriazole development inhibitor releasing coupler, as described.

Synthesis of a coupler by the described method is illustrated as follows:

<u>Synthesis Example B:</u>

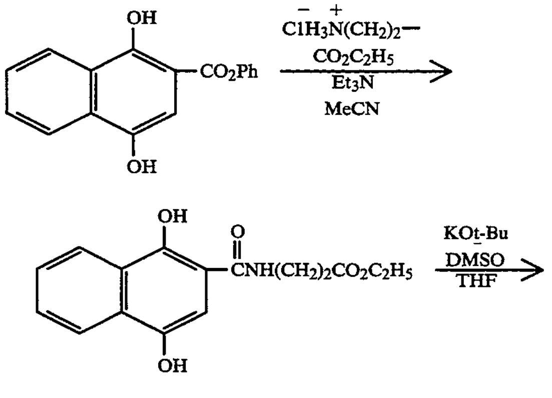

(B1)

-continued

Synthesis Example B:

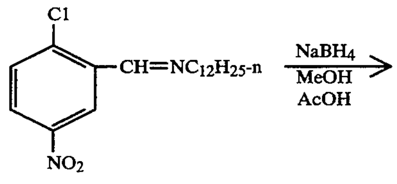

(B2)

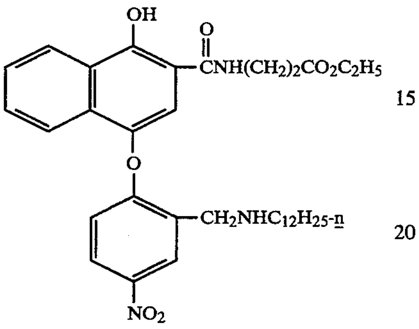

(B3)

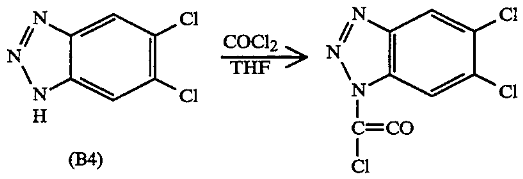

(B4)

(B5)

(B3) + (B5)

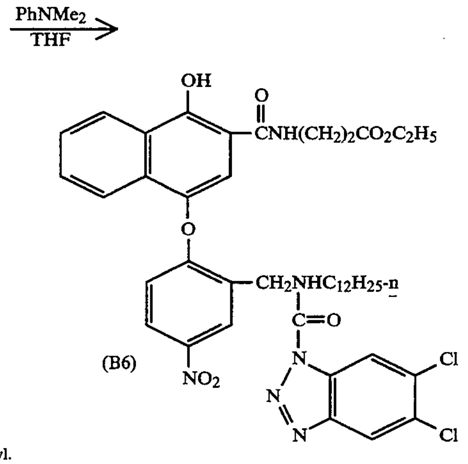

(B6)

Et herein is ethyl.
Me herein is methyl.
THF herein is tetrahydrofuran.
HOAc herein is acetic acid.
Ph herein is phenyl.

Compound (B1)

Phenyl 1,4-dihydroxy-2-naphthoate (28.0 g, 0.10 mol) and β-analine ethyl ester hydrochloride (30.7 g 0.20 mol) were mixed with acetonitrile (125 mL). The mixture was stirred at room temperature under a nitrogen atmosphere. A solution of triethylamine (20.2 g, 0.20 mol) in acetonitrile (60 mL) was added dropwise. After the addition was complete the mixture was heated to reflux for 2 hours. The mixture was allowed to cool to room temperature, then it was poured with stirring into a mixture of ice and water (1.0 L) and concentrated HCl (50 mL). The product came out of solution as a solid.

The aqueous mixture was filtered and the collected solid was washed with water. The product was sucked as dry as possible on the funnel then was transferred to a beaker. The material was stirred with warm water (≈400 mL) for 10 minutes. The mixture was filtered and the solid was washed with cold water. The product was dried in a vacuum oven under a nitrogen atmosphere at ≈45° for 24 hours. This gave a pale tan powder, m.p. 162°-165°. Yield 29.4 g

Compound (B2)

2-Chloro-5-nitrobenzaldehyde (55.5 g, 0.30 mol) and n-dodecylamine (55.5 g, 0.30 mol) were mixed with ethanol (300 mL). The mixture was stirred and heated to reflux for 2 hours. The resulting warm solution was allowed to cool at room temperature; the product crystallized out. The mixture was chilled in ice, then was filtered. The collected solid was washed with cold methanol. The product was dried in a vacuum oven under a nitrogen atmosphere at room temperature overnight. This gave a beige colored powder, m.p. 52°-54°. Yield 88.7 g (84%).

Compound (B3)

Compound (B1) (24.2 g, 0.08 tool) and compound (B2) (28.2 g, 0.08 tool) were mixed with dry dimethylsulfoxide (DMSO) (300 mL) and dry tetrahydrofuran (60 mL). The mixture was stirred under a nitrogen atmosphere and was warmed to ≈35° with a hot water bath. All (B1) and (B2) went into solution. The heating bath was removed and the mixture was stirred at room temperature. Potassium L-butoxide (19.8 g, 0.0176 mol) was added in portions over 15 minutes while keeping the pot temperature between 30°-35°. The resulting dark red solution was stirred for 2 hours at room temperature. Ethyl acetate (300 mL) and methanol (30 mL) were added to the mixture. The mixture was cooled to 0°-5° with an ice-salt bath. Sodium borohydride (4.0 g, 0.105 mol) was added in portions over 10 minutes. The mixture was stirred for 15 minutes, then the pH of the mixture was adjusted to ≈7 by adding acetic acid (10 mL). The mixture was stirred 2 hours at 0°-5°, then at room temperature overnight.

Water (100 mL) was added and the mixture was stirred ≈15 minutes. The reaction mixture was transferred to a separatory funnel. Ethyl acetate (≈300 mL) and water (≈300 mL) were added and the layers were allowed to separate. The organic layer was washed 3 times with water (≈200 mL portions) and once with saturated sodium chloride solution (≈250 mL). The ethyl acetate solution was dried over magnesium sulfate. This mixture was filtered through a pad of basic alumina. The solvent was removed from the filtrate on a rotary evaporator. The resulting reddish-brown oil was dissolved in ethanol (110 mL). This solution was stirred at room temperature overnight; a solid separated out. The mixture was chilled in ice, then was filtered. The collected solid was washed with cold ethanol, then with pentane. The product was dried in a vacuum oven at ≈40° under nitrogen for several hours. This gave compound (B3) a yellow powder, m.p. 101°-105°. Yield 21.8 g (44%).

Compound (B5)

Compound (B4) (14.0 g, 0.075 mol) was mixed with dry tetrahydrofuran (135 mL). The mixture was stirred at room temperature under a nitrogen atmosphere to form a slurry. Phosgene (18% solution in toluene, 98 mL, 0.098 mol) was added dropwise over 30 minutes. All (B4) dissolved as the addition proceeded. After the addition was complete the solution was stirred at room temperature for 17 hours. The solvent was removed on a rotary evaporator. The residue was dissolved in dichloromethane (≈200 mL). The solvent was again removed on a rotary evaporator. The remaining solid residue was slurried with pentane. The mixture was filtered and the product was dried in a vacuum oven at room temperature under a nitrogen atmosphere. This gave compound (B5) as a beige powder, m.p. 125°-128°. Yield 16.7 g (89%).

Compound (B6)

Compound (B3) (10.0 g, 0.016 mol) and N,N-dimethylaniline (9.7 g, 0.080 mol) were mixed with dry tetrahydrofuran (100 mL). The mixture was stirred at room temperature under a nitrogen atmosphere and a solution of compound (B5) (5.0 g, 0.020 mol) in tetrahydrofuran (75 mL) was added dropwise over 30 minutes. The resulting solution was stirred at room temperature for 1 hour. At this point TLC (silica gel-ethyl acetate/heptane; 30:70) showed a major product spot at Rf 0.55. The reaction mixture was poured with stirring into a mixture of ice and water (800 mL) plus hydrochloric acid (80 mL). The aqueous mixture was extracted 2 times with ethyl acetate. The extracts were combined and were washed 2 times with saturated sodium chloride solution. The extracts were dried over magnesium sulfate and then were filtered. The solvent was removed on a rotary evaporator to give a pale orange semi-solid. This material was dissolved in warm ethyl acetate (50 mL) and was chromatographed on a silica gel column (2.5 L) using ethyl acetate/heptane (25:75) as the eluant. The fractions containing the desired product were combined and the solvent was removed on a rotary evaporator. This gave a beige solid which was recrystallized from acetonitrile. The product was a beige powder, m.p. 133°-135°.Yield 8.8 g (66%). High pressure liquid chromatography showed the presence of one isomer (95.1%).

Calculated For: $C_{42}H_{48}Cl_2N_6O_8$: C, 60.35; H, 5.75; N, 10.05; Cl, 8.48 Found: C, 59.95; H, 5.54;N, 9.77; Cl, 8.19

Examples of other couplers that can be prepared are as follows:

I-1

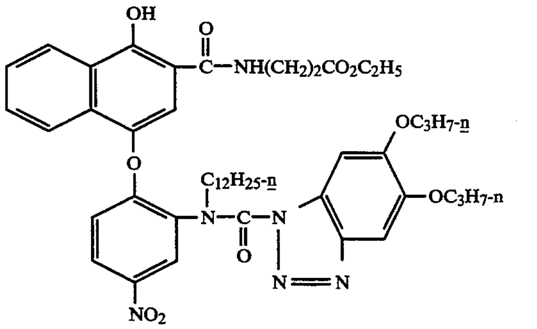

-continued

I-2

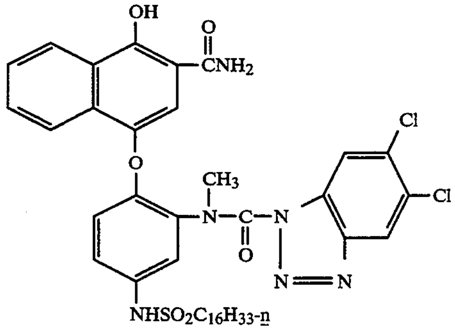

I-3

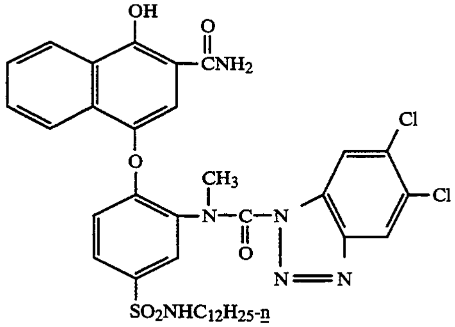

I-4

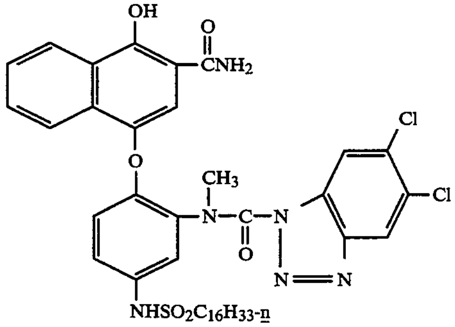

I-5

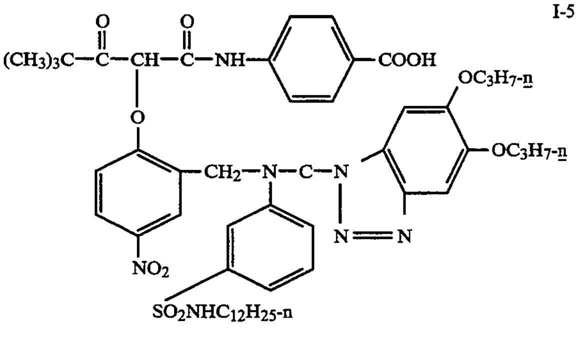

I-6

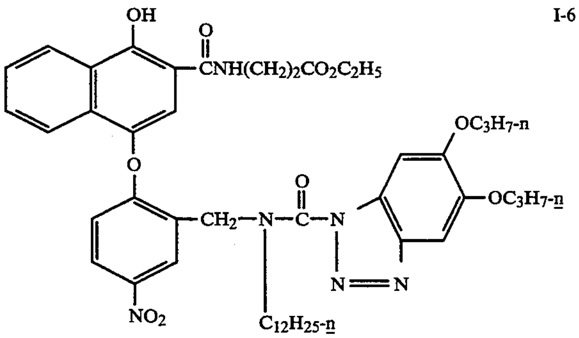

-continued

I-7

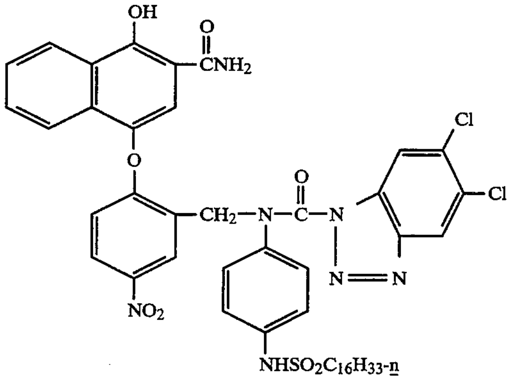

I-8

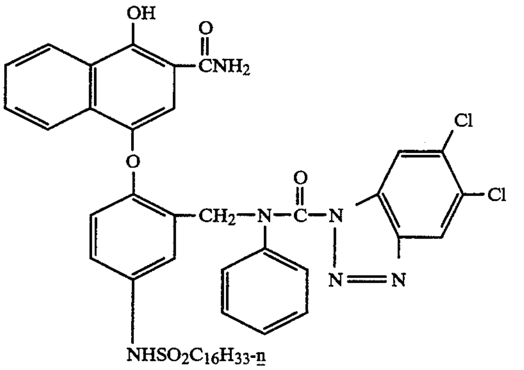

I-9

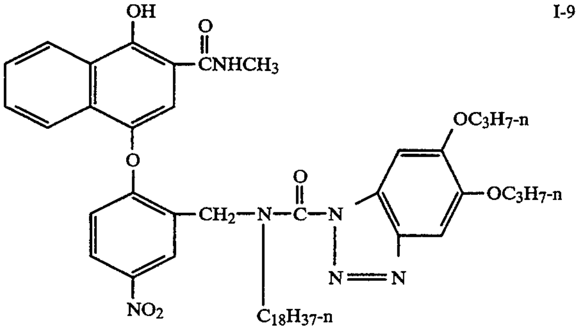

I-10

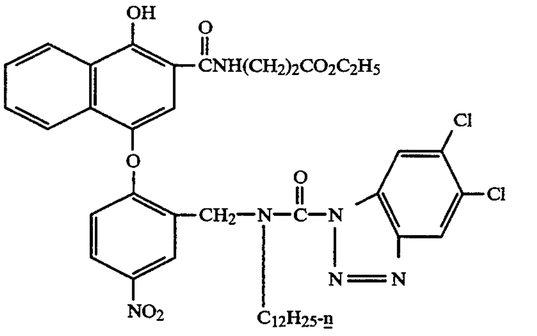

-continued

I-11

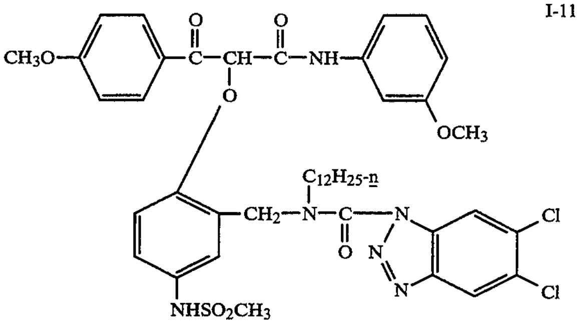

Example 1

A color photographic recording material (comparative sample A) for color negative development was prepared by applying the following layers in the given sequence to a transparent cellulose triacetate film support. The quantities of silver halide are given in mg of silver per $ft^2$. The quantities in "( )" are in mg per $m^2$. All silver halide emulsions were stabilized with 2 grams of 4-hydroxy-6-methyl-1,3,3a,7-tetraazaindene per mole of silver.

Layer 1 (Antihalation Layer)

Black colloidal silver sol containing 22 mg (236) of silver and 227 mg (2440) gelatin.

Layer 2 (First Red-Sensitive Layer)

Red sensitized silver iodobromide emulsion (3.0 mol percent iodide, average grain diameter 0.6 microns) at 50 mg (538), red sensitized silver iodobromide emulsion (4.5 mol percent iodide, average grain diameter 1.2 microns) at 80 mg (860), cyan dye-forming image coupler C-1 at 100 mg (1075), DIR compound D-1 at 3 mg (32) with gelatin at 300 mg (3225).

Layer 3 (Second Red-Sensitive Layer)

Red sensitized silver iodobromide emulsion (4.0 mol percent iodide, average grain diameter 2.3 microns) at 150 mg (1612), cyan dye-forming image coupler C-1 at 35 mg (376), DIR compound D-1 at 3.8 mg (41) with gelatin at 250 mg (2688).

Layer 4 (Interlayer)

Oxidized developer scavenger S-1 at 5 mg (54), with 100 mg (1075) gelatin.

Layer 5 (First Green-Sensitive Layer)

Green sensitized silver iodobromide emulsion (3.3 mol percent iodide, average grain diameter 0.58 microns) at 30 mg (322), green sensitized iodobromide emulsion (2.0 mol percent iodide, average grain diameter 1.1 microns) at 75 mg (806), magenta dye-forming image coupler M-1 at 50 mg (538), DIR compound D-2 at 2.5 mg (27) with gelatin at 230 mg (2473).

Layer 6 (Second Green-Sensitized Layer)

Green sensitized silver iodobromide emulsion (2 mol percent iodide, average grain diameter 1.48 microns) at 115 mg (1236), magenta dye-forming image coupler M-2 at 18 mg (194), DIR compound D-2 at 1.3 mg (14) with gelatin a 230 mg (2473).

Layer 7 (Interlayer)

Oxidized developer scavenger S-1 at 5 mg (54), yellow colloidal silver at 6 mg (65) with gelatin at 100 mg (1075).

Layer 8 (First Blue-Sensitive Layer)

Blue sensitized silver iodobromide emulsion (1.1 mol percent iodide, average grain diameter 0.60 microns) at 25 mg (269), blue sensitized silver iodobromide emulsion (2.4 mol percent iodide, average grain diameter 2.15 microns) at 40 mg (430), yellow dye-forming image coupler Y-1 at 75 mg (806), DIR compound D-3 at 3 mg (33) with gelatin at 150 mg (1612).

Layer 9 (Second Blue-Sensitive Layer)

Blue sensitized silver iodobromide emulsion (12 mol percent iodide, average grain diameter 2.01 microns) at 75 mg (806), yellow dye-forming image coupler Y-1 at 12 mg (129) with gelatin at 150 mg (1612).

Layer 10 (Protective Layer)

110 mg (1183) of gelatin with 2% by weight to total gelatin of hardener H-1.

Compounds M-1, M-2 and D-2 were used as emulsions containing tricresylphosphate; compounds C-1, Y-1 and D-3 were used as emulsions containing di-n-butyl phthlate; while compound D-1 was used as an emulsion containing N-n-butyl acetanilide.

Photographic comparative sample A incorporates a magenta dye-forming DIR compound (D-2) known in the art (from U.S. Pat. No. 3,615,506).

Additional photographic samples were prepared in an analogous manner except that various DIR compounds were substituted for DIR D-2 in the fast magenta layer (second green-sensitive layer #6) and in the slow magenta layer (first green-sensitive layer #5). The quantities of the various DIR compounds were selected to provide a green dye gamma of approximately 0.65 after a white light exposure and color processing as described below.

Photographic comparative sample B incorporates a cyan dye-forming DIR compound (D-4) known in the art (from U.S. Pat. No. 4,248,962).

These samples were exposed either to white light, red light (using a Kodak Wratten 29 filter) or green light (using a Kodak Wratten 74 filter) through a grey wedge chart. These samples were then developed using a color negative process, the KODAK C-41 process, as described in the British Journal of Photography Annual of 1988, pp. 196–198. (Kodak and Wratten are trademarks of Eastman Kodak Company, U.S.A.).

The stability of the compounds was monitored by storing film samples for four weeks at a temperature of 38° C. and at a relative humidity of 50%. The samples were then developed as described earlier and the increase in green fog density was monitored. All of the inventive compounds show excellent stability.

The formulas of the described couplers are as follows:

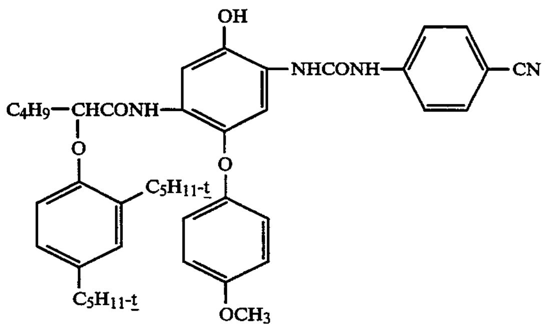

C-1

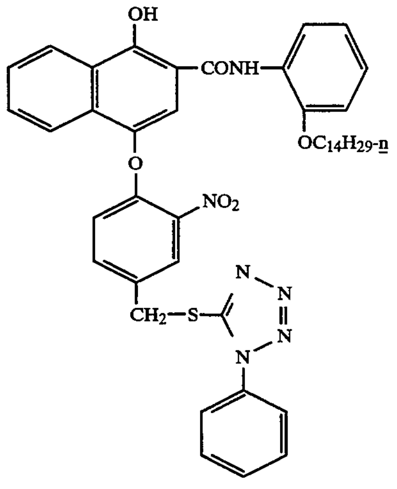

D-1

-continued
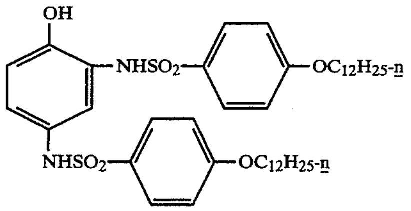
S-1
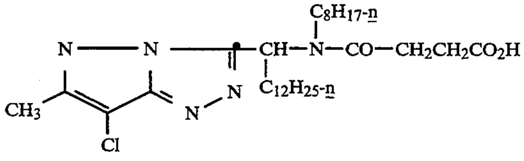
M-1
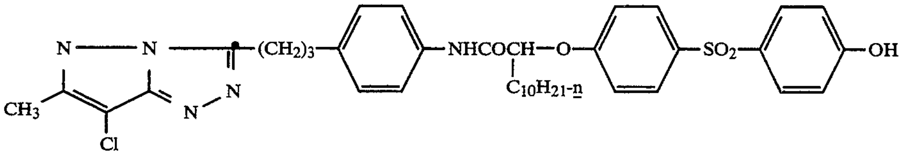
M-2
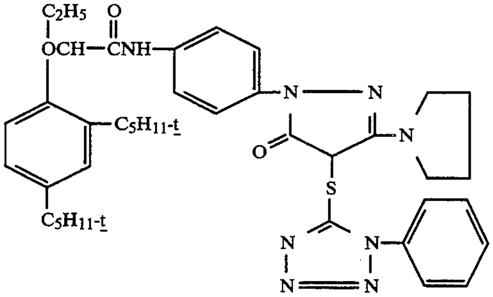
D-2
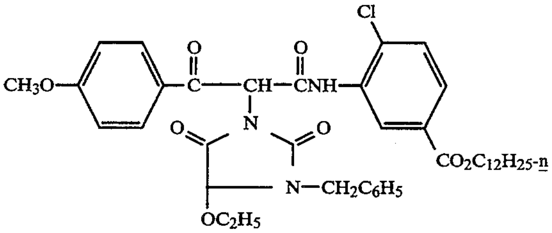
Y-1
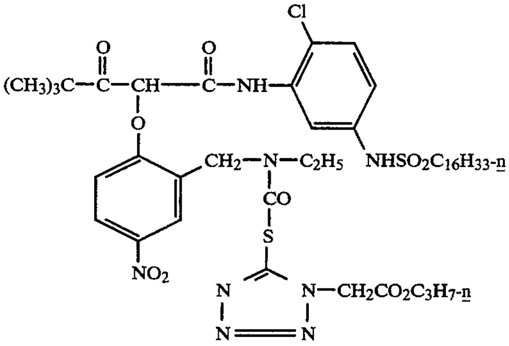
D-3

-continued

D-4

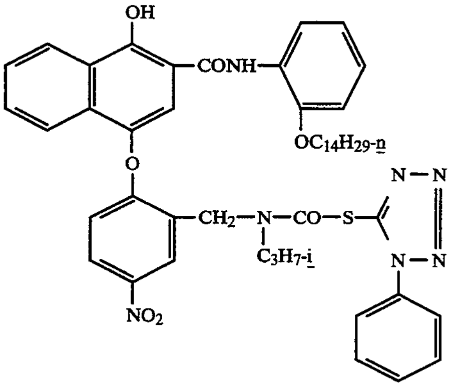

The following DIR coupler provided useful improved sharpness and stability in a color photographic element and processing as described.

-continued

| | |
|---|---|
| Overcoat | bisvinylsulfonylmethyl ether at 2% total gelatin. |

EXAMPLES 2–5

Magenta Image Coupler M-3:

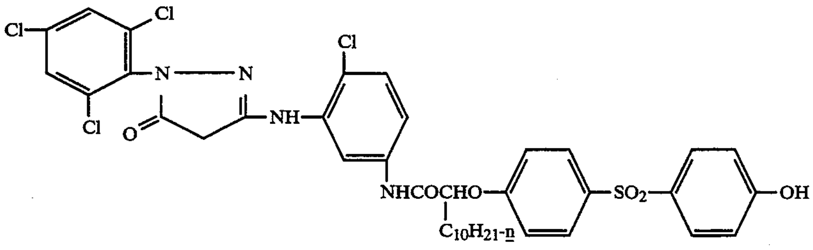

Yellow Image Coupler Y-2:

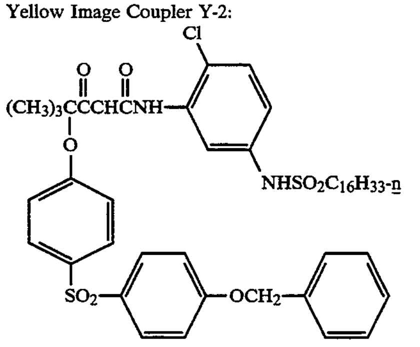

Photographic elements were prepared by coating the following layers on a cellulose ester film support (amounts of each component are indicated in mg/m²):

| | |
|---|---|
| Emulsion layer 1: | Gelatin - 2691; red sensitized silver bromoiodide (as Ag) - 1615; yellow dye-forming image coupler Y-2 dispersed in dibutyl phthalate (RECEIVER LAYER) |
| Interlayer: | Gelatin - 624; didodecylhydroquinone - 113 |
| Emulsion layer 2: | Gelatin; green sensitized silver bromoiodide (as Ag) - 1615; magenta dye-forming image coupler M-3 dispersed in dibutyl phthalate; DIR compound of Table I dispersed in N,N-diethyl-dodecanamide and coated at a level sufficient to provide a contrast to green light of 0.5 of the original contrast after stepwise green light exposure and processing. (CAUSER LAYER) |
| Protective: | Gelatin - 5382; |

Structures of the image couplers are as follows:

Strips of each element were exposed to green light through a graduated density step table, or through a 35% modulation fringe chart for sharpness measurements, and then developed 3.25 minutes at 38° C. in the following color developer, stopped, washed, bleached, fixed, washed and dried.

| Color Developer: | | |
|---|---|---|
| Distilled water | 800 | mL |
| Sulfuric acid | 2.0 | ml |
| Potassium Sulfite | 2.0 | g |
| CD-4 | 3.35 | g |
| Potassium Carbonate | 30.0 | g |
| Potassium Bromide | 1.25 | g |
| Potassium Iodide | 0.6 | mg |
| Distilled water | to 1 | L |
| Adjust pH to 10.0 | | |

CD-4 is 4-amino-3-methyl-N-ethyl-N-beta-hydroxy-ethylaniline sulfate.

Processed images were read with green light to determine the contrast and AMT acutance. From plots of AMT acutance vs. the logarithm of the contrast for variations in the coated level of each development inhibitor releasing (DIR) compound, the acutance was determined at a contrast of 0.5 of its original contrast without the presence of the DIR compound. The acutance values are reported in following Table I. AMT calculations employed the following formula in which the cascaded area under the system modulation curve is shown in equation (21.104) on page 629 of the "Theory of the Photographic Process", 4th Edition, 1977, edited by T. H. James: AMT=100+66 Log[cascaded area/2.6696M] wherein the magnification factor M is 3.8 for the 35 mm system AMT. The use of CMT acutance is described by R. G. Gendron in "An Improved Objective method of Rating Picture Sharpness: CMT acutance" in the Journal of SMPTE, Vol. 82, pages 1009-12, (1973). AMT is a further modification of CMT useful for evaluating systems which include the viewing of a positive print made from a negative.

Interlayer interimage effects were evaluated by calculating the ratio of causer layer dye gamma to receiver layer dye gamma. This analysis is described in U.S. Pat. No. 4,248,962. A larger value of the ratio indicates a greater interlayer interimage effect.

Color purity was evaluated by measuring the status M red density of the coating after processing. A smaller value indicates a greater degree of color purity.

TABLE I

| Example No. | DIR Compound | $AMT_{35}$ | Change in $AMT_{35}$ | Gamma Causer / Gamma Receiver | Red Density |
|---|---|---|---|---|---|
| A (Comparison) | D-5 | 93.6 | 0 | 1.9 | 0.28 |
| B " | D-6 | 93.6 | 0 | 1.9 | 0.28 |
| C " | D-7 | 93.1 | −0.5 | 2.1 | 0.41 |
| D " | D-2 | 93.6 | 0 | 2.1 | 0.24 |
| 2 (invention) | I-9 | 96.0 | +2.4 | 2.2 | 0.25 |
| 3 " | I-6 | 95.8 | +2.2 | 2.0 | 0.28 |
| 4 " | I-10 | 95.5 | +1.9 | 3.4 | 0.33 |
| 5 " | I-7 | 96.8 | +3.2 | 2.7 | 0.25 |

D-5

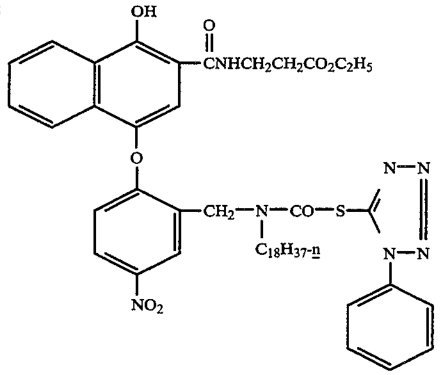

D-6

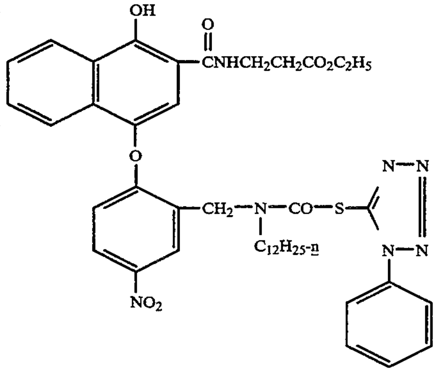

D-7

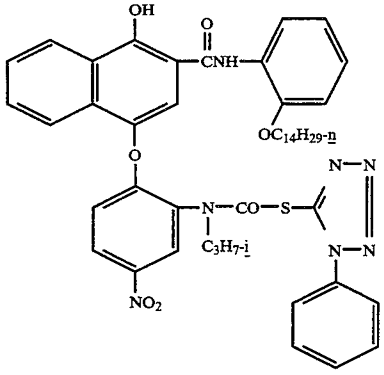

The invention has been described in detail with particular reference to preferred embodiments thereof, but it will be understood that variations and modifications can be effected within the spirit and scope of the invention.

What is claimed is:

1. A color photographic element comprising a support bearing at least one photographic silver halide emulsion layer and at least one benzotriazole development inhibitor releasing naphtholic wash-out coupler which forms a dye that is capable of being washed out of the photographic element upon processing comprising an amide water solubilizing group in the 2-position of the naphthol moiety wherein the benzotriazole development inhibitor is represented by the formula:

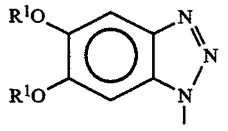

wherein $R^1O$ is an unsubstituted alkoxy group.

2. A color photographic element comprising a support bearing at least one photographic silver halide emulsion layer and at least one benzotriazole development inhibitor releasing naphtholic wash-out coupler which forms a dye that is capable of being washed out of the photographic element upon processing comprising an amide water solubilizing group selected from $CONH_2$ and $CONHCH_3$ in the 2-position of the naphthol moiety wherein the benzotriazole development inhibitor is represented by the formula:

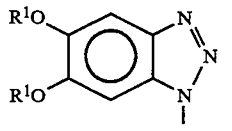

wherein $R^1O$ is an unsubstituted alkoxy group.

3. A color photographic element as in claim 2 wherein the benzotriazole development inhibitor releasing coupler is represented by the formula:

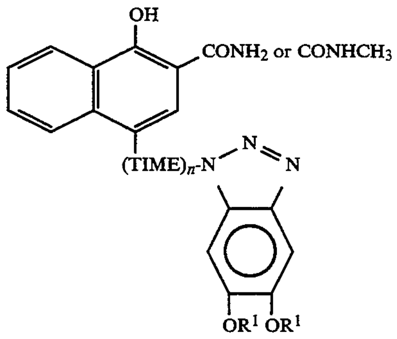

wherein $OR^1$ is an unsubstituted alkoxy group;

TIME is a photographic timing group; and n is 0, 1 or 2.

4. A color photographic element as in claim 3 wherein TIME comprises a ballasted carbamate group.

5. A color photographic element as in claim 2 wherein the amide water solubilizing group is $—CONH_2$.

* * * * *